United States Patent [19]
Kato et al.

[11] Patent Number: 5,654,440
[45] Date of Patent: Aug. 5, 1997

[54] METHOD FOR PRODUCTION OF OPTICALLY ACTIVE (+)-4,4,4-TRIFLUORO-3-(INDOLE-3-)BUTYRIC ACID

[75] Inventors: Katsuya Kato; Shozo Fujii; Masato Katayama, all of Nagoya; Hiroshi Kimoto, Kuwana, all of Japan

[73] Assignee: Agency of Industrial Science & Technology, Ministry of International Trade & Industry, Tokyo, Japan

[21] Appl. No.: 616,462

[22] Filed: Mar. 15, 1996

[30] Foreign Application Priority Data

Jun. 7, 1995 [JP] Japan ................................ 7-164813

[51] Int. Cl.$^6$ .................................................. C07D 209/18
[52] U.S. Cl. .................................................. 548/494
[58] Field of Search ................................... 548/494

[56] References Cited

U.S. PATENT DOCUMENTS 5,496,794  3/1996  Katayama et al. .
5,578,552  11/1996  Katayama et al. .................. 504/285

FOREIGN PATENT DOCUMENTS 5-279331  10/1993  Japan .
6-56774   3/1994   Japan .

OTHER PUBLICATIONS

Katsuya Kato, et al., "Enzymatic Preparation of Both Enantiomers of 4,4,4–Trifluoro–3–(Indole–3–)Butyric Acid, a Novel Plant Growth Regulator", Journal of Fermentation and Bioengineering, vol. 76, No. 3, (pp. 178–183), 1993.

*Primary Examiner*—Jacqueline Haley
*Attorney, Agent, or Firm*—Oblon, Spivak, McClelland, Maier & Neustadt, P.C.

[57] ABSTRACT

An optically active (+)-4,4,4-trifluoro-3-(indole-3-)butyric acid is produced by a method which consists essentially of causing 2,2,2-trifluoroethanol to react on a racemic modification 4,4,4-trifluoro-3-(indole-3-)butyric acid thereby forming a reaction solution containing the trifluoroethyl ester of the butyric acid, causing an enzyme having an esterase activity to act on the reaction solution thereby forming an optically active (+)-4,4,4-trifluoro-3-(indole-3-) butyric acid, and thereafter separating the reaction product from the reaction solution.

11 Claims, No Drawings

METHOD FOR PRODUCTION OF OPTICALLY ACTIVE (+)-4,4,4-TRIFLUORO-3-(INDOLE-3-)BUTYRIC ACID

BACKGROUND OF THE INVENTION

1. Field of the Invention

This invention relates to a method for the production of an optically active (+)-4,4,4-trifluoro-3-(indole-3-butyric acid. More particularly, this invention relates to a method for the production of an optically active (+)-4,4,4,-trifluoro-3-(indole-3-)butyric acid having a strong action of promoting the elongation of plant roots, by preparing a 2,2,2-trifluoroethyl ester of 4,4,4-trifluoro-3-(indole-3-)butyric acid as a racemic modification and subjecting the ester to stereoselective hydrolysis using an enzyme.

The optically active (+)-4,4,4-trifluoro-3-(indole-3-)butyric acid (hereinafter referred to as "optically active (+)-TFIBA") is one of the fluorine-containing β-indole butyric acids and has plant growth regulating activities such as the action of promoting the elongation of plant roots.

The optically active (+)-TFIBA is thus an important compound which functions as a plant growth regulating substance and can be extensively applied in agriculture and horticulture as for increasing crop yield and the cultivation of fruits.

2. Description of the Prior Art

As auxins, i.e. substances which promote the growth of plants, indole-3-acetic acid (IAA) and derivatives thereof (such as indole-3-methyl acetate and indole-3-acetamide) have been known for a long time.

Recently, such compounds as fluorine-containing β-indole butyric acids have been developed. These compounds, i.e. 4,4,4-trifluoro-3-(indole-3-)butyric acid (hereinafter referred to as "TFIBA"), 4,4,4-trifluoro-2-hydroxy-3-(indole-3-)butyric acid, and 4,4,4-trifluoro-3-(indole-3-)butyronitrile, have been shown to have a strong action of promoting the elongation of plant roots (Japanese Patent Public Disclosure Hei 5-279331).

It is further known that the optically active (+)-TFIBA is obtained by causing an enzyme to react on an ethyl ester of a racemic modification TFIBA containing an asymmetric carbon atom thereby effecting selective hydrolysis of the ester and that this product of hydrolysis has a stronger action of promoting the elongation of roots than the racemic modification TFIBA. It is known that among enzymes studied to date, lipase PS, lipase AK, lipase AY, and protease M are suitable for producing the optically active (+)-TFIBA and that particularly when the lipase AK is used, the optically active (+)-TFIBA is formed at high stereoselectivity and high optical purity [Japanese Patent Public Disclosure Hei 6-56774, J. Fermentation and Bioengineering 76:178 (1993)].

The racemic modification TFIBA has a fairly strong action of promoting the elongation of plant roots as described above. It is known that the enzymatically divided optically active (+)-TFIBA has a still stronger activity, namely a still stronger action of promoting the elongation of roots. Since the conventional enzymatically dividing method is deficient in the reactivity between enzyme and substrate, it is therefore desired to establish a more efficient enzymatically dividing method.

SUMMARY OF THE INVENTION

The present inventors continued a study with a view to developing such a method and, as a consequence, have perfected this invention.

To be specific, the optically active (+)-TFIBA is obtained with high selectivity and yield and considerably more quickly and efficiently than by the conventional method by synthesizing a compound represented by the formula (2):

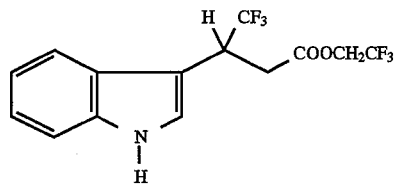

from a racemic modification TFIBA represented by the formula (1):

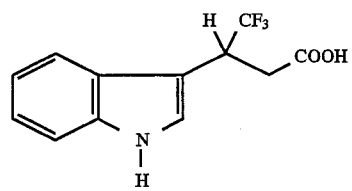

and hydrolyzing the compound of the formula (2) by the use of an enzyme.

This invention is directed to a method for the production of an optically active (+)-4,4,4-trifluoro-3-(indole-3-)butyric acid, which essentially consists of causing 2,2,2-trifluoroethanol to react on a racemic modification, 4,4,4-trifluoro-3-(indole-3-)butyric acid, represented by the formula (1):

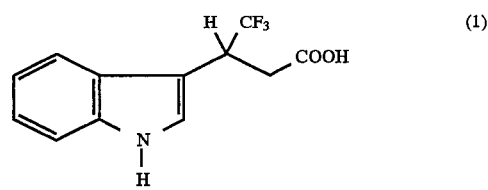

thereby forming an ester represented by the formula (2),

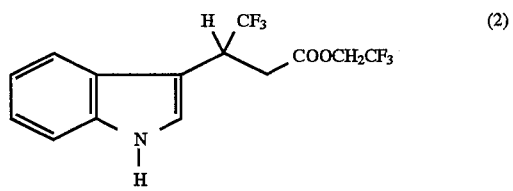

adding a buffer solution to the resultant ester, causing an enzyme having an esterase activity to react on the produced solution containing the ester thereby forming an optically active (+)-4,4,4-trifluoro-3-(indole-3-)butyric acid represented by the formula (3):

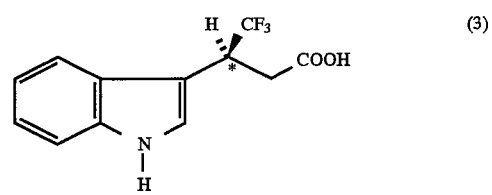

and then isolating the optically active (+)-4,4,4-trifluoro-3-(indole-3-)butyric acid from the resultant reaction solution.

DESCRIPTION OF THE PREFERRED EMBODIMENTS

The racemic modification, TFIBA, represented by the formula (1) and used as the raw material in the method of this invention is produced by methods known to the art.

As one example of such a method that disclosed in Japanese Patent Public Disclosure Hei 5-279331 is described below.

A solution of dimethyl malonate in toluene and metallic sodium added thereto are refluxed and then added with 2,2,2-trifluoro-1-(indole-3-)ethanol. The resultant mixture is refluxed, added with water, and extracted with ethyl acetate. The ethyl acetate layer consequently formed is washed with water and a saturated aqueous solution of common salt, dried over anhydrous sodium sulfate, and then concentrated under a reduced pressure to obtain a crude toluene solution of dicarboxylic diester. This solution is distributed with hexane-acetonitrile and the acetonitrile layer is concentrated under a reduced pressure. The crude diester consequently obtained is dissolved in methanol, added with an aqueous solution of potassium carbonate, and refluxed. The resultant mixture is neutralized with hydrochloric acid, concentrated under a reduced pressure to expel methanol, alkalinized with an aqueous 4N sodium hydroxide solution, and then extracted with ethyl acetate. The water layer consequently formed is acidified with hydrochloric acid and extracted with ethyl acetate. The ethyl acetate layer is washed with water and a saturated aqueous solution of common salt, and dried over anhydrous sodium sulfate. The crude carboxylic acid obtained in consequence of the concentration under a reduced pressure is refined by silica gel column chromatography to obtain 4,4,4-trifluoro-3-(indole-3-)butyric acid.

In the method of this invention, when an enzyme having an esterase activity is made to react on the reaction solution containing the ester represented by the formula (2), this ester is optically selectively hydrolyzed.

The chemical reactions involved in the production of the optically active (+)-TFIBA (3) from the racemic modification TFIBA (1) are shown below.

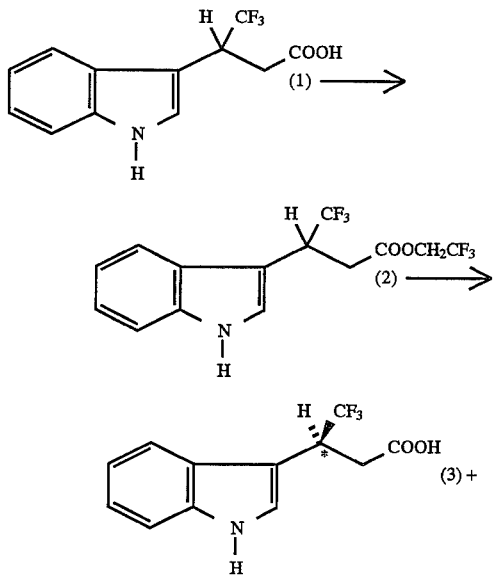

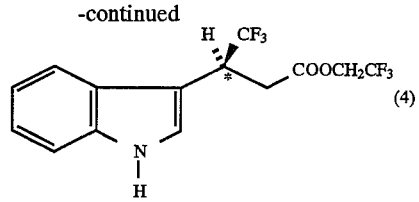

Enzymes having an esterase activity that can be advantageously used in this invention include lipases and/or proteases. Lipases produced by genus Pseudomonas such as, for example, Lipase PS (product of Amano Pharmaceutical Co., Ltd.) and Lipase AK (product of Amano Pharmaceutical Co., Ltd.) and lipases produced by genus Candida such as, for example, Lipase AY (product of Amano Pharmaceutical Co., Ltd.) are preferably used as lipases and proteases produced by genus Aspergillus such as, for example, Protease M (product of Amano Pharmaceutical Co., Ltd.) are preferably used as proteases. The enzyme to be used may be a crude product or a refined product. The microbial cells which produce these enzymes may be utilized.

The asymmetric hydrolyric reaction by the use of an enzyme which has an esterase activity proceeds advantageously in the presence of a suitable buffer solution and/or an organic solvent. The buffer solution to be used in this case is required to fit the working pH of the enzyme being used for the reaction. To be specific, phosphate buffer solution, acetate buffer solution, glycine buffer solution, etc. are used, for example.

As the organic solvent, any of the organic solvents which are in popular use can be adopted on the condition that they do not hinder the enzymatic reaction. Particularly, t-butyl alcohol, hexane, acetone, DMF (dimethylformamide), tetrahydrofuran, t-amyl alcohol, etc. can be advantageously used. The concentration of the organic solvent used in combination with the buffer solution in the enzymatic reaction is in the range of 0.2 to 50%, preferably 0.5 to 30%.

As regards the conditions for the enzymatic reaction, the reaction temperature is in the range of 0° to 70° C., preferably 30° to 50° C., and the reaction time in the range of 0.2 to 500 hours, preferably 1 to 10 hours.

The separation of the optically active (+)-4,4,4-trifluoro-3-(indole-3-)butyric acid from the reaction solution can be easily implemented by known methods.

The optically active (+)-TFIBA (3) which is obtained as described above has a powerful action of elongating roots. When this product is used as a plant growth regulating agent, it is used in its unmodified form or, for the purpose of promoting or stabilizing the effect thereof, used in the form of liquid, powder, granules, wettable powder, flowable agent, or emulsion as mixed with suitable adjuvants which are popular use in agricultural pesticides.

These preparations may be used either directly or as diluted with water to prescribed concentrations.

The compound represented by the formula (3) can be generally used at concentrations in the range of $1 \times 1/10^8$ to $1 \times 1/10^2 M$, though this range is not critical.

This invention will now be described more specifically below with reference to working examples and a referential example. It should be noted, however, that this invention is not limited to these examples.

EXAMPLE 1

Production of Racemic Modification TFIBA-2,2,2-trifluoroethyl Ester (2) by the Method of this Invention In dichloromethane (40 ml), racemic modification TFIBA (1) (2 g, 7.8 mmols), 2,2,2-trifluroethanol (2.3 g, 23.4 mmols), DCC (dicyclohexyl carboxylimide) (2.4 g, 11.8 mmols), and DMPA (dimethylaminopyridine) (0.12 g, 1.0 mmol) were stirred to react at room temperature for three hours. The reaction solution consequently formed was concentrated and separated by silica gel chromatography (dichloromethane). The separated concentrate was recrystallized from dichloromethane/hexane (3/7) to obtain colorless columnar crystals of racemic modification TFIBA-2,2,2-trifluoroethyl ester (2) (2.47 g, 93.6% of yield).

The melting point of this ester was 47.8° to 48.5° C. The infrared absorption spectrum and the mass spectrum of the ester were obtained. The results are shown below.

IR$v_{max}$KBr (cm$^{-1}$): 3400, 1760, 1460, 1320, 1280, 1170, 1120, 980, 960, 750

MS (70 eV): 339 (M$^+$, 10), 198 (41), 69 (100)

REFERENTIAL EXAMPLE

Production of Various Alkyl Esters of Racemic Modification TFIBA for Comparison

A racemic modification TFIBA (1) (5.1 g, 20 mmols) was dissolved in 300 ml of ethanol and the resultant solution was saturated with hydrogen chloride gas. The saturated solution was refluxed overnight, distilled to expel ethanol and hydrochloric acid by vaporization, and dried to solidification. The residue was refined by silica gel column chromatography and recrystallized from hexane to obtain a racemic modification TFIBA-ethyl ester represented by the following formula (2') (5.5 g, yield 96%).

[Structure (2'): indole with H and CF$_3$ substituent, CH-COOC$_2$H$_5$ group]

The melting point of this ester was 57°~58° C.

A racemic modification TFIBA-methyl ester, a racemic modification TFIBA-propyl ester, and a racemic modification TFIBA-isopropyl ester were produced by following the procedure described above. The yields and the melting points of these esters were as shown below.

Racemic modification TFIBA-methyl ester—98.5%, 87°~88° C.

Racemic modification TFIBA-propyl ester—83.9%, 54°~55° C.

Racemic modification TFIBA-isopropyl ester—77.4%, 47°-48° C.

EXAMPLE 2

The racemic modification TFIBA-2,2,2-trifluoroethyl ester (2) prepared in Example 1 and the alkyl esters of racemic modification TFIBA prepared in Reference Example (each 3.0 mg) were added with a phosphate buffer solution containing 10% t-butyl alcohol (pH 7.0, 3.0 ml) and Lipase AK (100 mg). The resultant suspensions were stirred to react at 30° C. for 5 to 330 hours to effect stereoselective hydrolysis of the esters. After the reaction, the suspensions were adjusted to pH 2 with a 1N hydrochloric acid and extracted three times with ethyl acetate. The extracts were dried over sodium sulfate and filtered. The filtrates were dried to solidification and analyzed by liquid chromatography (using a "Chiralcel OD" column manufactured by Daicel Ltd.) to determine formation of an optically active (+)-TFIBA (3). The results are shown in Table 1 below.

TABLE 1

| R | Time (hrs) | Conversion$^a$ (%) | ee(%)/recovery ratio (%) Acid | ee(%)/recovery ratio (%) Ester | E$^b$ |
|---|---|---|---|---|---|
| CH$_3$ | 90 | 43 | >99/43 | 74/56 | >100(S) |
| CH$_2$CH$_3$ | 90 | 43 | >99/43 | 75/57 | >100(S) |
| CH$_2$CH$_2$CH$_3$ | 90 | 47 | >99/49 | 87/51 | >100(S) |
| CH(CH$_3$)$_2$ | 330 | 10 | >99/10 | 11/90 | >100(S) |
| CH$_2$CF$_3$ | 5 | 51 | 95/50 | >99/49 | >100(S) |

$^a$Conversion = ee (ester)/{ee(ester) + ee(acid)} × 100
$^b$E value = ln[1 − c{1 + ee(acid)}]/ln[1 − c{1 − ee(acid)}]

According to Japanese Patent Public Disclosure Hei 6-56774 and J. Fermentation and Bioengineering 76, 178 (1993), a study on the selective optical resolution of ethyl esters (2') with an enzyme revealed that Lipase AK, a hydrolytic enzyme, has the highest activity.

The racemic modification TFIBA esters of Example 1 and Comparative Example were compared in reactivity by using Lipase AK under the optimum reaction conditions. The results clearly showed that the reaction velocity decidedly increased in the case of 2,2,2-trifluoroethyl ester (2).

EXAMPLE 3

Effect of Temperature and Organic Solvent on Stereoselective Hydrolysis of Racemic TFIBA-2,2,2-Trifluoroethyl Ester (2) with Lipase AK The racemic modification TFIBA-2,2,2-trifluoroethyl ester (2) (3 mg) prepared in Example 1 was added with a phosphate buffer solution containing one of six organic solvents at a concentration of 10% (pH 7.0, 3.0 ml), and Lipase AK (10 mg). The resultant suspension was stirred to react at 30°~50° C. for one to ten hours. Six species of organic solvents, used were t-butyl alcohol, hexane, acetone, DMF, tetrahydrofuran, and t-amyl alcohol. The reaction solutions consequently obtained were analyzed to determine formation of an optically active (+)-TFIBA (3). The results are shown in Table 2.

TABLE 2

| Organic solvent/°C. | Time (hrs) | Conversion$^a$ (%) | ee(%)/recovery ratio (%) Acid | ee(%)/recovery ratio (%) Ester | E$^b$ |
|---|---|---|---|---|---|
| t-Butyl alcohol/30 | 10 | 49 | >99/50 | 94/50 | >100(S) |
| t-Butyl alcohol/40 | 1 | 26 | >99/27 | 36/73 | >100(S) |
| t-Butyl alcohol/50 | 1 | 23 | >99/22 | 30/78 | >100(S) |
| Hexane/40 | 1 | 24 | >99/25 | 32/75 | >100(S) |
| Aceton/40 | 1 | 29 | >99/29 | 41/70 | >100(S) |
| DMF/40 | 1 | 44 | >99/45 | 79/55 | >100(S) |
| Tetrahydrofuran/40 | 1 | 49 | >99/48 | 94/52 | >100(S) |
| t-Amyl alcohol/40 | 1 | 50 | >99/51 | >99/48 | >100(S) |

$^a$Conversion = ee(ester)/{ee(ester) + ee(acid)} × 100
$^b$E value = ln[1 − c{1 + ee(acid)}]/ln[1 − c{1 − ee(acid)}]

These results clearly show that in all the solvents used the Lipase AK formed the optically active (+)-TFIBA (3) with high yields and that the reaction was completed in a short span of time when t-amyl alcohol was used as the solvent. Thus, t-amyl alcohol is preferably used for the reaction.

EXAMPLE 4

Effect of Repeated Use of Immobilized Lipase AK on Activity of Stereoselective Hydrolysis The racemic modification TFIBA-2,2,2-trifluoroethyl ester (2) (0.30 g) prepared in Example 1, a phosphate buffer solution containing 10% of t-amyl alcohol (pH 7.0, 300 ml), and Lipase AK (1 g) immobilized on cerite (4 g) were left reacting at 40° C. for one hour to determine formation of optically active (+)-TFIBA (3). The immobilized Lipase AK was then separated from the resultant reaction solution by filtration and used in its unmodified form to repeat the same reaction on newly supplied racemic modification TFIBA-2, 2,2-trifluoroethyl ester (2) to determine formation of an optically active (+)-TFIBA (3). Further, the immobilized Lipase AK separated again by filtration was used to repeat the same reaction to determine the formation and the effect of the repeated use of the immobilized Lipase AK on the activity of stereoselective hydrolysis. The results are shown in Table 3.

TABLE 3

| Number of repeated uses | Time (hrs) | Conversion[a] (%) | ee(%)/recovery ratio | | |
|---|---|---|---|---|---|
| | | | Acid | Ester | E[b] |
| 1 | 1.0 | 53 | 89/54 | >99/50 | >100(S) |
| 2 | 1.5 | 47 | >99/43 | 89/55 | >100(S) |
| 3 | 1.8 | 43 | >99/46 | 74/52 | >100(S) |

[a]Conversion = ee(ester)/{ee(ester) + ee(acid)} × 100
[b]E value = ln[1 − c{1 + ee(acid)}]/ln[1 − c{1 − ee(acid)}]

These results clearly show that the repeated use of the immobilized Lipase AK entailed a slight decrease of reactivity and that the immobilization of enzyme allowed repeated use of the enzyme used in a small amount and permitted production of the optically active (+)-TFIBA (3) with high stereoselectivity and a high yield.

EXAMPLE 5

Production of Optically Active (+)-TFIBA (3) in Acetate Buffer Solution

In an acetate buffer solution (pH 4.0, 450 ml) and t-butyl alcohol (50 ml), Lipase AK (15 g) was placed and stirred at 30° C. for 20 minutes. A racemic modification TFIBA-2,2, 2-trifluoroethyl ester (2) (0.5 g) was added to the resultant suspension and stirred at 30° C. for 60 hours. The reaction solution consequently formed was adjusted to pH 2.0 with an aqueous 1N hydrochloric acid solution and extracted three times with ethyl acetate (500 ml). The extract was dried over magnesium sulfate and distilled to expel the solvent by vaporization. The residue of distillation was refined by silica gel chromatography to obtain an optically active (+)-TFIBA (3) of an optical purity of 99% ee and an angle of rotation, $[\alpha]_D^{28}$, of +10.7° (c=0.9, EtOH) with a yield of 92%. At the same time, an optically active (−)- TFIBA-2,2,2-trifluoroethyl ester (4) of an optical purity of 99% ee and an angle of rotation, $[\alpha]_D^{28}$, of −12.9° (c=1.0, EtOH) was obtained with a yield of 93%.

What is claimed is:

1. A method for the production of an optically active (+)-4,4,4-trifluoro-3-(indole-3-)butyric acid, consisting essentially of the steps of causing 2,2,2-trifluoroethanol to react on a racemic modification 4,4,4-trifluoro-3-(indole-3-)butyric acid, represented by the formula (1):

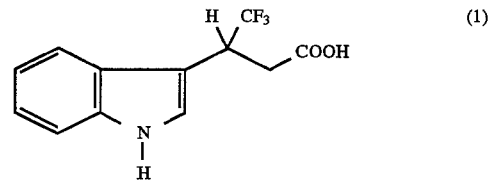

thereby forming an ester represented by the formula (2),

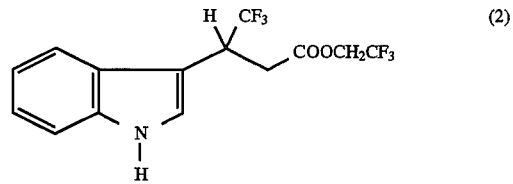

adding a buffer solution to the resultant ester, causing an enzyme having an esterase activity to react on the produced solution containing said ester thereby forming an optically active (+)-4,4,4-trifluoro-3-(indole-3-)butyric acid represented by the formula (3):

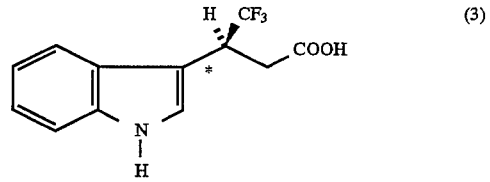

and then isolating the optically active (+)-4,4,4-trifluoro-3-(indole-3-)butyric acid from the resultant reaction solution.

2. The method according to claim 1, wherein said buffer solution is suitable for the working pH of the enzyme in use.

3. The method according to claim 1, wherein said buffer solution is one member selected from the group consisting of phosphate buffer solution, acetate buffer solution, and glycine buffer solution.

4. The method according to claim 1, wherein the reaction solution to be acted on by said enzyme contains an organic solvent.

5. The method according to claim 4, wherein said organic solvent is at least one member selected from the group consisting of t-butyl alcohol, hexane, acetone, dimethylformamide, tetrahydrofuran, and t-amyl alcohol.

6. The method according to claim 1, wherein the reaction solution to be acted on by said enzyme contains an organic solvent and a buffer solution and the concentration of said organic solvent is in the range of 0.2 to 50%, based on the concentration of said buffer solution.

7. The method according to claim 1, wherein the reaction of said enzyme is carried out at a temperature in the range of 0° to 70° C. for a period in the range of 2 to 500 hours.

8. The method according to claim 7, wherein said temperature is in the range of 30° to 50° C. and said period is in the range of 1 to 10 hours.

9. The method according to claim 1, wherein said enzyme is at least one member selected from the group consisting of lipases and proteases.

10. The method according to claim 9, wherein said lipase is at least one member selected from the group consisting of lipases produced by the microorganisms of genus Pseudomonas and genus Candida.

11. The method according to claim 9, wherein said protease is at least one member selected from the group consisting of proteases produced by the microorganisms of genus Aspergillus.

* * * * *